(12) United States Patent
Bajomi et al.

(10) Patent No.: US 9,314,016 B2
(45) Date of Patent: Apr. 19, 2016

(54) RODENT CONTROL DEVICE

(75) Inventors: Dániel Bajomi, Budapest (HU); János Daru, Budapest (HU); Attila Halasi, Budapest (HU); Vince Pozsár, Ács (HU); József Schmidt, Bicske (HU); János Szilágyi, Budapest (HU); László Takács, Budapest (HU); József Tomcsik, Budapest (HU)

(73) Assignee: BÁBOLNA KOÖRNYEZETBIOLOÖGIAI KÖZPONT KFT., Budapest (HU)

( * ) Notice: Subject to any disclaimer, the term of this patent is extended or adjusted under 35 U.S.C. 154(b) by 0 days.

(21) Appl. No.: 14/374,608

(22) PCT Filed: Jan. 27, 2012

(86) PCT No.: PCT/HU2012/000007
§ 371 (c)(1),
(2), (4) Date: Jul. 25, 2014

(87) PCT Pub. No.: WO2013/110962
PCT Pub. Date: Aug. 1, 2013

(65) Prior Publication Data
US 2014/0341840 A1    Nov. 20, 2014

(51) Int. Cl.
*A01M 25/00* (2006.01)
*A01N 25/00* (2006.01)
(Continued)

(52) U.S. Cl.
CPC ............ *A01N 25/004* (2013.01); *A01M 25/00* (2013.01); *A01N 25/34* (2013.01); *A01N 33/18* (2013.01);
(Continued)

(58) Field of Classification Search
CPC ....... A01N 43/16; A01N 25/34; A01N 33/18; A01N 25/004; A01N 2300/00; A01M 25/00; B29C 47/0004; B29C 47/065; B29K 2091/00; B29K 2105/0011; B29L 2031/737
See application file for complete search history.

(56) References Cited

U.S. PATENT DOCUMENTS 3,917,658 A * 11/1975 Feather et al. ............... 552/631
4,891,218 A    1/1990 Sherman
(Continued)

FOREIGN PATENT DOCUMENTS

BE    904052    7/1986
BE    904203    8/1986
(Continued)

OTHER PUBLICATIONS

International Search Report issued in PCT/HU2012/000007, mailed on Nov. 28, 2012.
(Continued)

*Primary Examiner* — Aradhana Sasan
(74) *Attorney, Agent, or Firm* — Birch, Stewart, Kolasch & Birch, LLP

(57) ABSTRACT

The present invention relates to a device for controlling rodents. More specifically, the present invention relates to a device consisting of a combination of a solid and a pulpy bait (commonly known as 'fresh bait' or ' paste bait' in rodent control practice), wherein the solid part is a shaped paraffinized rodenticide bait with a rodenticide concentration which is lower than or equal to the rodenticide concentration of the combination and contains the pulpy rodenticide bait with a rodenticide concentration which is higher than or equal to the rodenticide concentration of the combination. The rodent control device according to the invention has an enhanced acceptance by the rodents and can preferably be fixed by a hole formed in the solid part preventing the rodents to take it away. Furthermore, the present invention relates to the preparation and use of such rodent control device.

28 Claims, 3 Drawing Sheets

(51) Int. Cl.
  *A01N 25/34*  (2006.01)
  *A01N 33/18*  (2006.01)
  *A01N 43/16*  (2006.01)
  *B29C 47/00*  (2006.01)
  *B29C 47/06*  (2006.01)
  *B29K 91/00*  (2006.01)
  *B29K 105/00* (2006.01)
  *B29L 31/00*  (2006.01)

(52) U.S. Cl.
  CPC ............ *A01N 43/16* (2013.01); *B29C 47/0004* (2013.01); *B29C 47/065* (2013.01); *B29K 2091/00* (2013.01); *B29K 2105/0011* (2013.01); *B29L 2031/737* (2013.01)

(56) References Cited

U.S. PATENT DOCUMENTS

2005/0181003 A1* 8/2005 Endepols et al. ............. 424/410
2006/0057178 A1* 3/2006 Borchert et al. ............. 424/408

FOREIGN PATENT DOCUMENTS

| EP | 0 475 551 A2 | 3/1992 |
| EP | 2 090 164 A1 | 8/2009 |
| EP | 2 497 362 A1 | 9/2012 |

OTHER PUBLICATIONS

PCT/ISA/237—Issued in PCT/HU2012/000007, mailed on Nov. 28, 2012.

* cited by examiner

RODENT CONTROL DEVICE

The present invention relates to a device for controlling rodents. More specifically, it relates to a device consisting of a combination of a solid and a pulpy bait (commonly known as 'fresh bait' or pasta 'paste bait' in rodent control practice), wherein the solid part is a shaped paraffinized rodenticide bait with a rodenticide concentration which is lower than or equal to the rodenticide concentration of the combination and contains the pulpy rodenticide bait with a rodenticide concentration which is higher than or equal to the rodenticide concentration of the combination. The rodent control device according to the invention has an enhanced acceptance by the rodents and can preferably be fixed by a hole formed in the solid part preventing the rodents to take it away. Furthermore, the present invention relates to the preparation and use of such rodent control device.

As a result of the multiplication of rodent populations over the past decades, the control of rodents, especially mice and rats, has become a well-known issue of high importance. Besides health concerns and especially in bigger cities, issues about rodents include major damage in food storages, and they may be carriers of diseases which affect both humans and farm animals.

Over the years, various attempts have been made to control rodents and numerous methods have been developed, including physical and chemical methods.

Physical methods include the use of mechanical devices such as glues, traps (e.g., see EP 0599755 A1, EP 1149530 A2) and electric devices, these letter killing rodents via electric shocks (e.g., see WO 99/018780).

In general, chemical methods refer to devices containing a rodenticide poison (hereinafter also referred to as "rodenticide active ingredient" or "rodenticide") in a carrier edible for rodents. During the past years, several types of chemical baits for indoor and outdoor domestic uses have been placed onto the market. These products may have various consistencies. The main types of products include:

Solid products, in which rodenticide active ingredients are added to a composition consumable by rodents, such as cereal and/or fruit aggregates, milling products, flours, and mixtures containing animal parts, especially insect parts. In order to increase acceptance/palatability, such compositions also contain aromas, flavours, vegetable oils, fruits, fish, sugar and the like. It is also well-known that such baits may contain colouring agents, preservatives and bittering substances (repellents). The main reason for adding the latter is to prevent human consumption, especially consumption by children.

One group of solid products includes products based on milled cereals (loose baits). Although milled cereal based products are especially effective rodenticides, they have the disadvantage of being easily spilled and thus may cause major environmental pollution.

BE 904052 and BE 904203 discloses rodenticide products based on fresh fruits, roots or vegetables for use as baits, which contain the rodenticide active ingredient in one or more holes inside a tube-like case. Such products include drilled carrots, sugar-beets, beetroots and the like. Such solutions have the disadvantage of making it possible for the rodent to consume the food favourable to it without necessarily getting at the poison-containing internal core. Another drawback is that they are mostly limited to hand-made preparation and uses while their industrial scale production and shelf-lives may be problematic.

Another form of solid poisonous baits are paraffin-wax-based products in which the rodenticide active ingredient and other components are mixed with paraffin wax. These are generally produced in the form of blocks. For example, U.S. Pat. No. 4,891,218 discloses a paraffinized rodenticide bait block, wherein the physical structure and shape of the block, such as the ridged surface and edges, ensure effective consumption by the rodent and, therefore, the rodenticide effect. Preferably, the dimensions of the block are selected in a manner to provide sufficient amounts of poison to kill an average-sized rodent.

One advantage of paraffinized products is their solid state; therefore, they can be easily fixed and rodents cannot take it away from the place of application. In addition, they are more resistant to humidity than the products packed in cellulose bags and thus may be used in humid environments, too. However, one disadvantage of paraffin wax is that rodents do not like it and it reduces the acceptance/palatability of the bait. Another drawback is that in known extruded paraffinized blocks the concentration of the active ingredient is the same on the surface and inside, therefore, nothing reduces the exposure and poisoning resulting from regular or long-term contact with the bait.

Another type of products includes pulpy products also known as paste products. Typically, pulpy products contain elevated levels of attractive oils and fats of high nutritional value, therefore, they are highly acceptable and tasteful for rodents. In order to prevent rancidity, antioxidants are also typically added to these products. Pulpy baits are generally available in sachets and this results in considerable amounts of the rodent-attracting oil content to ooze out of the sachet during the warm summer months; thus, it becomes unattractive to the rodent, difficult to handle, and with increased risk of contamination for the user and the environment. Another important disadvantage of pulpy baits is the difficulty or impossibility to fix them, and rodents will take them away to their hiding places which results in environmental pollution via scattering. By creating a possibility for undesired consumption of the rodenticide-containing baits, such scattered baits may present a risk to non-target organisms such as farm animals.

Known products also include combined products containing a synergistic combination of active ingredients to increase their killing efficiency. For example, EP 2090164 A1 discloses a rodenticide bait containing a synergistic combination of two anticoagulant ingredients, preferably in the form of paraffinized blocks.

EP 1279334 discloses a combined bait with rat killing effect, which contains a rodenticide active ingredient and a bait composition, wherein the bait composition contains a component tasteful for rodents in a paste form, which contains flour of animal and/or plant origin, i.e., a solid component suitable for chewing. Preferably, this solid component is selected from the group of cereals, expanded cereals, fruits, vegetables and flour aggregates, wherein the fruits and vegetables are present in small, preferably dried pieces. Basically, the claimed combined bait mix is an improved pulpy bait prepared by first dispersing one part of the rodenticide active ingredient in a liquid carrier, such as glycol, mixing it with the solid bait component, preferably in a pulper equipment, and then letting it stand for a time to allow the rodenticide active ingredient to be absorbed by the solid component. Next, powder-like components are added to the rest of the rodenticide active ingredient under continuous mixing, and the mixture is then let stand for 45 to 60 minutes to ensure even dispersion of the rodenticide active ingredients. The obtained bait is filled into single-dose filter paper sachets. Therefore, this method essentially produces a pulpy bait in which chewable food pieces—which are either milled to a grain size coarser than that of flour or unmilled—are dispersed. This is also demonstrated by the examples, in which the specified mixes contain 58% to 60% crop/animal flours, 15% whole, expanded grains and fruit/vegetable granulates and 18% to 20% fat-like materials. The rodenticide active ingredient is evenly dispersed in the coarse (middling sized) solid bait component and the flour-containing pulpy bait. Although the data presented herein suggest that rats consume the combined bait very well, the risk of scattering still remains due to the sachet packaging.

Accordingly, there is still a great need for new rodenticide products that eliminate the disadvantages of the above-mentioned types.

One objective of the present invention is to provide a rodent control device which is highly attractive for and fully consumable by rodents, even in the presence of usual foods.

Another objective of the invention is to provide a rodent control device which effectively kills a wide range and the largest number of rodents, and, at the same time, is fixable and thus cannot be taken away, thereby having a lower potential for environmental pollution and undesired poisonous effects.

Another objective of the invention is to provide a rodent control device which presents less risks to all those qualified and unqualified individuals that come into contact with it than the known paraffinized products. In general, it presents lower risks than the rodenticide active ingredients which are non-individually packaged in materials impermeable for the rodenticide, and containing one dose for a single application, as well as than the grain or coarse baits, which get easily spilled.

The above objectives can be achieved by the rodent control device of the present invention. Our experiments suggested that combining a solid paraffinized bait with a pulpy bait in a manner that the pulpy bait having a rodenticide concentration which is greater than or equal to the overall rodenticide concentration of the system is comprised in the shaped paraffinized solid bait having a rodenticide concentration which is less than or equal to the overall rodenticide concentration of the system and selecting the appropriate ratio of these main ingredients will result in a product of the desired active ingredient levels, which rodents will readily start to consume and will rapidly arrive to the delicious pulpy bait and, by consuming that, to the lethal dose.

The use of lower active ingredient levels in the external rigid part has the further advantage of reducing the risk of poisoning those handling the rodenticide product when in contact with it.

Accordingly, the object of the present invention is a rodent control device, which is a combination of a solid and a pulpy bait, wherein the solid part is a shaped paraffinized rodenticide bait with a rodenticide concentration lower than that of the combination, said solid part comprising the pulpy rodenticide bait having a rodenticide concentration higher than that of the combination.

Another object of the present invention is a rodent control device, which is a combination of a solid and a pulpy bait, wherein the solid part is a shaped paraffinized rodenticide bait with a rodenticide concentration equal to that of the combination, said solid part comprising the pulpy rodenticide bait having a rodenticide concentration equal to that of the combination.

In the rodent control device of the present invention, the percentage rate of the solid part and of the pulpy part compared to the total mass of device is preferably 70-90 for the one part and 10-30 for the other, more preferably 75-87 and 13-25 and most preferably 86.6 and 13.4.

In the rodent control device according to the invention, the ratio of the active ingredient in the solid part and in the pulpy part may be 1:1 to 1:70.

The combined rodenticide bait according to the invention is different from that described in EP 1279334 on several points; among others, the solid part is shaped, paraffin-containing and fixable; the solid bait and the pulpy bait components are not in the form of mixtures but the two types of baits, that is, the solid bait and the pulpy bait are definitively separate from each other; the concentration of the rodenticide active ingredient is different in the two bait components, that is, the solid part and the pulpy part contains rodenticide active ingredients in lower and higher levels, respectively, and the appearance of the combined bait is also different from the known product.

The solid bait component of the rodent control device of the invention comprises paraffin, wax and/or tallow, as well as an edible oil, grained, pressed, expanded, granulated or milled cereals, crops in the form of groats or flour, maize, rodenticide active ingredient, a sweetening agent, a preservative, dried and milled insects, and fruit pieces and vegetable aggregates. The solid component may contain colouring agents to prevent human consumption, and repellent agents such as denatonium benzoate, which are repulsive to humans and farm animals. The amount of the solid bait component is 70% to 90% (w/w) of the total mass of the rodent control device. Depending on the type of rodenticide ingredient, the solid bait component comprises the rodenticide in an amount of 0.0001% to 0.1% (w/w) of the total mass of the rodent control device.

The pulpy bait component of the rodent control device according to the invention is well accepted by rodents and contains cereal flours, oils/fats of plant origin and/or oils/fats of animal origin, an antioxidant, such as butyl hydroxyanisole, butyl hydroxytoluene, Vitamin A, Vitamin C, Vitamin E, flavours and/or aromas attractive for rodents, taste intensifiers such as salt, glutamic acid and salts thereof, guanic acid and salts thereof, inosinic acid and salts thereof, maltol and esters thereof, a sweetening agent, milled insects and a rodenticide active ingredient. The pulpy component may contain colouring agents, preferably with colours different from that of the solid bait part to prevent human consumption, and repellent agents such as denatonium benzoate, which are repulsive to humans and farm animals. The amount of the pulpy bait component is 10% to 30% (w/w) of the total mass of the rodent control device. Depending on the type of rodenticide ingredient, the pulpy bait component comprises the rodenticide in an amount of 0.0001% to 0.3% (w/w) of the total mass of the rodent control device.

The rodenticide active ingredient used in the rodent control device of the invention may be an acute rodenticide, that is, a poison such as scilliroside, strychnine, crimidine, bromethalin, sodium fluoroacetate, fluoroacetamide, zinc phosphide, norbormide, thallium sulphate, alpha-chloralose and alpha-naphthyltiourea or a mixture thereof; or it can be a chronic rodenticide, that is, a first generation anticoagulant such as warfarin, warfarin sodium, coumachlor, coumatetralyl, coumafuryl, pivaldione, diphacinone, chlorophacinone or a mixture thereof; or a second generation anticoagulant such as bromadiolone, diphenacoum, brodifacoum, difethialone and flocoumaphen or a mixture thereof.

In a preferred embodiment of the invention, the rodent control device comprises acute rodenticides, preferably bromethalin. In another preferred embodiment of the invention, anticoagulants are used as rodenticides, more preferably first or second generation anticoagulants, and most preferably, warfarin or bromadiolone.

In order to delay or prevent the development of tolerance or later resistance to the rodenticide in the rodents, various rodenticides can be used in the rodent control device according to the invention, for example, by providing different rodenticides within the same type in the solid part and in the pulpy part, or by providing different types of rodenticides in the solid part and in the pulpy part. In a preferred embodiment of the invention, the rodent control device comprises first and second generation anticoagulants, e.g., warfarin and bromadiolone.

The rodenticide ingredient in the rodent control device of the invention is dispersed in a manner that only 8% to 70% of the total permitted amount (50 ppm) is mixed into the solid bait and the remaining part, preferably 30% to 92% is used in the pulpy part. This will ensure that the rodent will rapidly consume the paraffinized solid part, but will also quickly arrive to the pulpy part because of the relatively thin walls of the holes that accommodate the pulpy part, and therefore, will consume a lethal dose of the active ingredient.

The shaped, paraffinized solid part of the rodent control device of the invention can be prepared in various forms, using any of the several known methods, preferably extrusion. FIGS. 1 to 6 show preferred embodiments of the invention.

Figure 1:
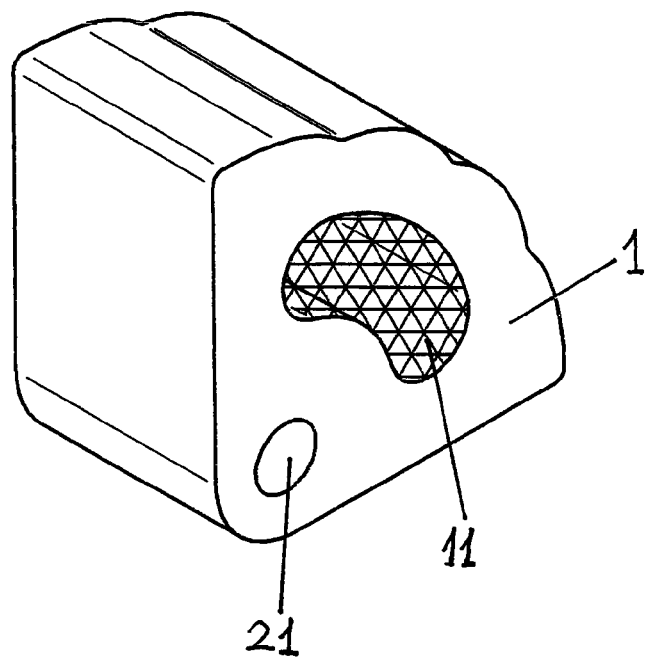
FIG. 1 shows a rodent control device, wherein the shaped rodenticide bait (1) is an extruded block with a circle-segment cross-section, and comprising one hole (11) for accommodating the pulpy rodenticide bait and another hole (21) for fixing.
Figure 2:
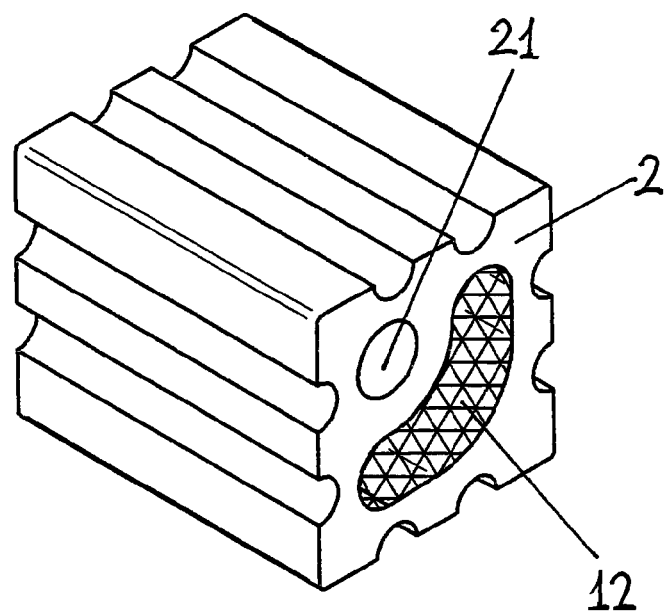
FIG. 2 shows a rodent control device, wherein the shaped rodenticide bait (2) is an extruded block with a rectangle cross-section provided with half-circle shaped hollows, and comprising one hole (12) for accommodating the pulpy rodenticide bait and one fixing hole (21).
Figure 3:
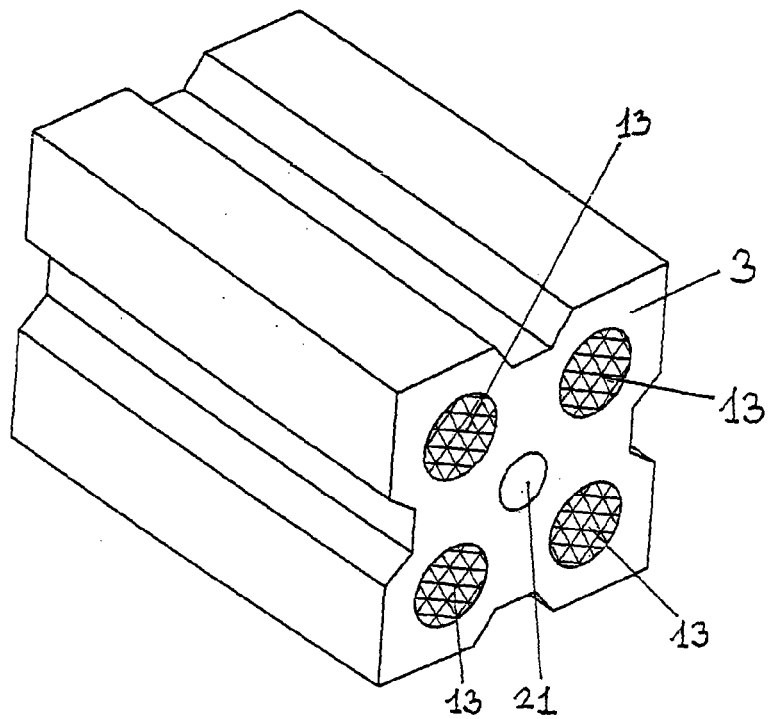
FIG. 3 shows a rodent control device, wherein the shaped rodenticide bait (3) is an extruded block with a rectangle cross-section provided with trapezoid hollows on all four sides, and comprising four holes (13) for accommodating the pulpy rodenticide bait and one fixing hole (21).
Figure 4:
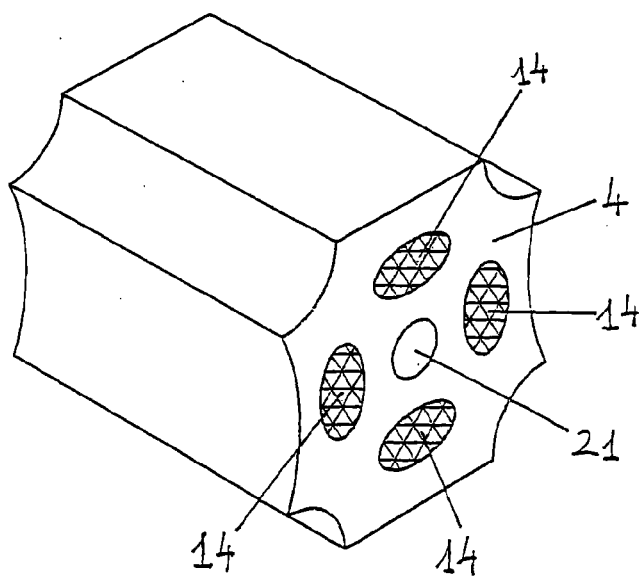
FIG. 4 shows a rodent control device, wherein the shaped rodenticide bait (4) is an extruded block with a rectangle cross-section provided with half-circle shaped hollows, and comprising four holes (14) for accommodating the pulpy rodenticide bait and one fixing hole (21).
Figure 5:
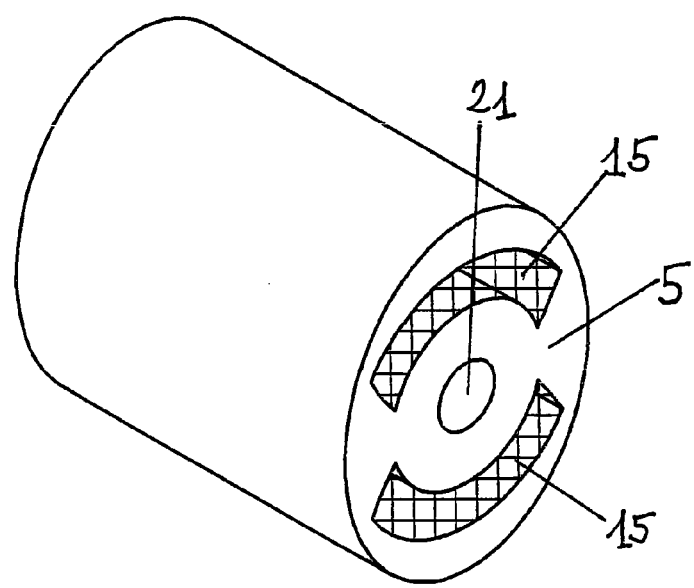
FIG. 5 shows a rodent control device, wherein the shaped rodenticide bait (5) is an extruded block with a circular cross-section, and comprising two holes (15) for accommodating the pulpy rodenticide bait and one fixing hole (21).
Figure 6:
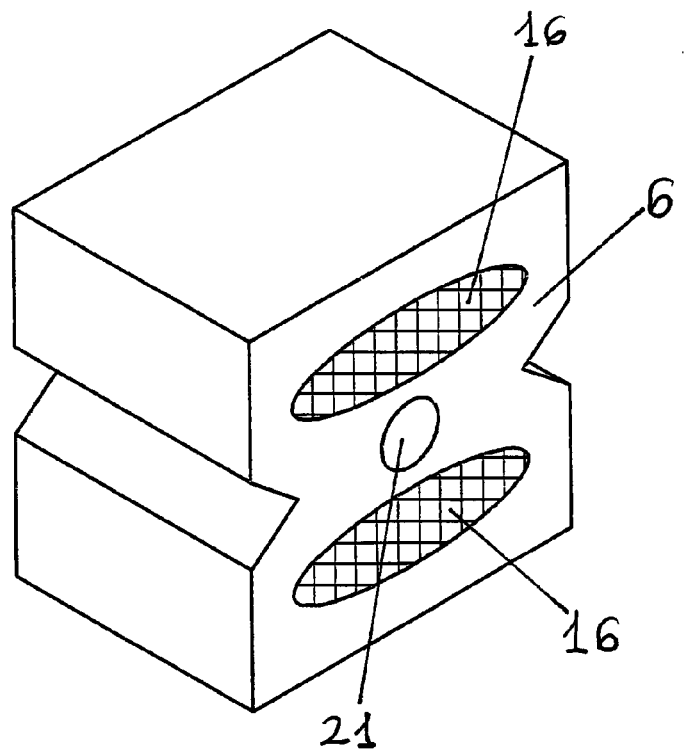
FIG. 6 shows a rodent control device, wherein the shaped rodenticide bait (6) is an extruded block with a rectangle cross-section provided with wedge shaped hollows, and comprising two holes (16) for accommodating the pulpy rodenticide bait and one fixing hole (21).

For example, the solid part of the rodent control device according to the invention is a block with rectangular cross-section provided with hollows and with one or more holes for the pulpy bait and at least one hole for fixing.

The rodent control device according to the invention is preferably fixable. For example, it can be placed onto a fixing rod via the fixing hole (21), wherein the fixing rod can be placed and fixed in a closed space, e.g. in a box or a bait station. The opening of the closed space can be provided in a manner to ensure that only rodents can access the fixed rodent control device. Fixing the device in this manner is preferred because rodents cannot take it away, and it will become inaccessible for other organisms after closing the box or bait station, and this will further increase safety. Another advantage of fixing is that rodents will be unable to take the bait away and this reduces the potential for environmental pollution.

Consumption and efficacy studies were conducted using brown rats (*Rattus norvegicus*), i.e., the most common species, to determine whether the rodent control devices of the invention are superior to the widely accepted standard composition comprising no rodenticide (hereinafter referred to as "EPA Standard"). The results demonstrate that the consumption increases significantly, approximately by 52% in comparison with the standard composition (see Example 9), and the mortality is also expected to increase because higher rodenticide amounts will accumulate in the body of the rodents within shorter periods, and they will consequently die earlier. Thus, the rodent control device according to the invention may reduce the time required for rodents to die. Therefore, by the use of the rodent control device of the invention, elimination of the rodent populations will require less time, bait, labour-force and maintenance.

The rodent control device of the invention has many advantages over the known paraffinized and pulpy products, including the above-mentioned combined products:
 efficient to kill a wide range and great numbers of rodents without polluting the environment or having secondary poisoning effects;
 in comparison with the known paraffinized blocks, consumption of the device is increased, and due to the feeding habits of the rodents (the bait is fixed and cannot be taken away) it produces a higher mortality and rodents will die earlier;
 the paraffinized solid part has lower rodenticide levels than the known extruded paraffinized blocks (e.g., PROTECT extruded rodenticide block), therefore, anyone having contact with it during application will be exposed to a lower risk of poisoning;
 in order to degrade acceptance/palatability, paraffin wax is only used in the amounts necessary for solidification and plasticity;
 rodents will quickly arrive to the highly nutritious pulpy bait with greater rodenticide levels;
 since rodents cannot take the device away, consumption can be easily tracked and checked.

According to another aspect, the invention also relates to the preparation of the rodent control device. The method of preparing the rodent control device consists of the steps of mixing the components of the paraffinized solid bait, shaping it into the desired form using methods that are known per se, such as extrusion or compression, and then pressing the separately prepared pulp part into the holes of the solid part. In another method, the pulpy part is filled in during the shaping of the solid part, for example, by coextrusion. For the preparation of the pulpy part, the fats and/or oils are mixed with the active ingredient, the antioxidant and the colouring agent in a suitable mixer. Other necessary components are admixed after a short incubation period.

According to a third aspect, the invention also relates to the use of the rodent control device for the control of rodents, especially rats and mice. Preferably, the rodent control device of the invention can be used for the control of harmful rodents belonging to the family of murine animals (Muridae), such as house mouse (*Mus musculus*), steppe mouse (*Mus spicilegus*), striped field mouse (*Mus agrarius* Pall), forest mouse (*Apodemus silvatica*), and rats, such as black rat (*Rattus rattus*) and brown rat (*Rattus norvegicus*).

The invention is more specifically described in the following examples which are provided as illustration only and will not limit the scope of the invention in any way.

Example 1

Preparation of a Rodent Control Device

A) Composition of the Solid Bait:

| Component | Amount % (w/w) |
|---|---|
| Warfarin: | 0.0038% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.1702% |
| | 100.000% |

B) Composition of the Pulpy Part:

| Component | Amount % (w/w) |
|---|---|
| Warfarin: | 0.2583% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.7387% |
| | 100.000% |

The rodent control device is prepared as follows: for the preparation of the solid part, from among the components listed under section A) the active ingredient is dissolved in the solvents, and then added to the mixture of the other components previously prepared in a suitable equipment, mixed to homogeneity, extruded separately and filled with the pulpy part or coextruded with the pulpy part.

For the preparation of the pulpy part, from among the components listed under section B) the active ingredient is dissolved in the solvents, then the fats and/or oils, the antioxidant and the colouring agent are added and mixed in a suitable mixer. Other necessary components are admixed after a short incubation period. However, the amount of both A) and B) are selected to ensure 86.6% (w/w) solid part and 13.4% (w/w) pulpy part in the rodent control device (with a total weight of 100%). The combined overall concentration of the rodenticide ingredient in the solid part and in the pulpy part is 0.038% (w/w).

Example 2

Preparation of a Rodent Control Device

A) Composition of the Solid Bait:

| Component | Amount % (w/w) |
|---|---|
| Warfarin: | 0.030% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.144% |
| | 100.000% |

B) Composition of the Pulpy Part:

| Component | Amount % (w/w) |
|---|---|
| Warfarin: | 0.0895% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.9075% |
| | 100.000% |

The method of preparing the rodent control device is exactly the same as described in Example 1. The amount of both A) and B) are selected to ensure 86.6% (w/w) solid part and 13.4% (w/w) pulpy part in the rodent control device (with a total weight of 100%). The combined overall concentration of the rodenticide ingredient is 0.038% (w/w).

Example 3

Preparation of a Rodent Control Device

A) Composition of the Solid Bait:

| Component | Amount % (w/w) |
|---|---|
| Bromadiolone: | 0.0005% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.1735% |
| | 100.000% |

B) Composition of the Pulpy Part:

| Component | Amount % (w/w) |
|---|---|
| Bromadiolone: | 0.034% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |

| Component | Amount % (w/w) |
| --- | --- |
| Fats/oils: | 25.000% |
| Solvents: | 3.963% |
| | 100.000% |

The method of preparing the rodent control device is exactly the same as described in Example 1. The amount of both A) and B) are selected to ensure 86.6% (w/w) solid part and 13.4% (w/w) pulpy part in the rodent control device (with a total weight of 100%). The combined overall concentration of the rodenticide ingredient is 0.005% (w/w).

Example 4

Preparation of a Rodent Control Device

A) Composition of the Solid Bait:

| Component | Amount % (w/w) |
| --- | --- |
| Bromadiolone: | 0.004% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.170% |
| | 100.000% |

B) Composition of the Pulpy Part:

| Component | Amount % (w/w) |
| --- | --- |
| Bromadiolone: | 0.0114% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.9856% |
| | 100.000% |

The method of preparing the rodent control device is exactly the same as described in Example 1. The amount of both A) and B) are selected to ensure 86.6% (w/w) solid part and 13.4% (w/w) pulpy part. The combined overall concentration of the rodenticide ingredient is 0.005% (w/w).

Example 5

Preparation of a Rodent Control Device

A) Composition of the Solid Bait:

| Component | Amount % (w/w) |
| --- | --- |
| Bromadiolone: | 0.003% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.171% |
| | 100.000% |

B) Composition of the Pulpy Part:

| Component | Amount % (w/w) |
| --- | --- |
| Bromadiolone: | 0.0098% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.9872% |
| | 100.000% |

The method of preparing the rodent control device is exactly the same as described in Example 1. The amount of both A) and B) are selected to ensure 70.5% (w/w) solid part and 29.5% (w/w) pulpy part. The combined overall concentration of the rodenticide ingredient is 0.005% (w/w).

Example 6

Preparation of a Rodent Control Device

A) Composition of the Solid Bait:

| Component | Amount % (w/w) |
| --- | --- |
| Bromadiolone: | 0.005% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.169% |
| | 100.000% |

B) Composition of the Pulpy Part:

| Component | Amount % (w/w) |
| --- | --- |
| Bromadiolone: | 0.005% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.992% |
| | 100.000% |

The method of preparing the rodent control device is exactly the same as described in Example 1. The amount of both A) and B) are selected to ensure 86.6% (w/w) solid part and 13.4% (w/w) pulpy part in the rodent control device. The combined overall concentration of the rodenticide ingredient is 0.005% (w/w).

Example 7

Preparation of a Rodent Control Device

A) Composition of the Solid Bait:

| Component | Amount % (w/w) |
|---|---|
| Bromethalin: | 0.001% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.173% |
| | 100.000% |

B) Composition of the Pulpy Part:

| Component | Amount % (w/w) |
|---|---|
| Bromethalin: | 0.068% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.881% |
| | 100.000% |

The method of preparing the rodent control device is exactly the same as described in Example 1. The amount of both A) and B) are selected to ensure 86.6% (w/w) solid part and 13.4% (w/w) pulpy part in the rodent control device. The combined overall concentration of the rodenticide ingredient is 0.01% (w/w).

Example 8

Preparation of a Rodent Control Device

A) Composition of the Solid Bait:

| Component | Amount % (w/w) |
|---|---|
| Bromethalin: | 0.009% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.165% |
| | 100.000% |

B) Composition of the Pulpy Part:

| Component | Amount % (w/w) |
|---|---|
| Bromethalin: | 0.0164% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.9806% |
| | 100.000% |

The method of preparing of the rodent control device is exactly the same as described in Example 1. The amount of both A) and B) are selected to ensure 86.6% (w/w) solid part and 13.4% (w/w) pulpy part in the rodent control device. The combined overall concentration of the rodenticide ingredient is 0.01% (w/w).

Example 9

Preparation of a Rodent Control Device

A) Composition of the Solid Bait:

| Component | Amount % (w/w) |
|---|---|
| Bromadiolone: | 0.0025% |
| Crop milling products/flours: | 62.998% |
| Sugar: | 8.000% |
| Antioxidant: | 0.072% |
| Flavours and aromas: | 0.600% |
| Preservatives: | 0.500% |
| Denatonium benzoate: | 0.002% |
| Colouring agent: | 0.024% |
| Paraffin wax: | 23.630% |
| Solvents: | 4.1715% |
| | 100.000% |

B) Composition of the Pulpy Part:

| Component | Amount % (w/w) |
|---|---|
| Warfarin: | 0.076% |
| Crop milling products/flours: | 66.658% |
| Sugar: | 4.000% |
| Antioxidant: | 0.093% |
| Flavours and aromas: | 0.150% |
| Preservatives: | 0.050% |
| Denatonium benzoate: | 0.002% |
| Colouring agent: | 0.050% |
| Fats/oils: | 25.000% |
| Solvents: | 3.921% |
| | 100.000% |

The method of preparing the rodent control device is exactly the same as described in Example 1. The amount of both A) and B) are selected to ensure 86.6% (w/w) solid part and 13.4% (w/w) pulpy part in the rodent control device. The concentration of the second generation rodenticide ingredient in the solid part is 0.003% (w/w), and the concentration of the first generation rodenticide ingredient in the pulpy part is 0.076% (w/w).

Example 10

Palatability (Consumption) Studies

Palatability studies were conducted with the rodent control device of the invention in comparison with the US EPA Standard (EPA: United States Environmental Protection Agency), which basically comprises crushed/milled crops (oat, corn) supplemented with sugar and edible oil, and no active ingredients. The studies were in compliance with the current guidelines and the habituation and pre-feeding periods were also observed.

Each study involved 5 male and 5 female, mature, healthy brown rats (Rattus norvegicus). Each rodent was accommodated separately in a 225×265×180 mm LF-3H type Amkrolon cage with a surface area of 800 mm². During the entire study, the temperature was set to 20° C. to 25° C. and the relative humidity to 45% to 50%, and the rodents were exposed to 12/12 hour dark/light periods. During the study, water was provided ad libitum.

After a three-day conditioning period, study rodents were given the usual CRLT/N laboratory feed (manufacturer: Bioplan Kft., Hungary) ad libitum. Two steel feeding containers were attached to both sides of the front of the cage; the first was filled with the experimental rodenticide product, and the second with the standard EPA feed. Three studies were conducted: in the first and second study the extruded solid part and the pulpy part were tested separately, while in the third one the combined rodent control device of the invention prepared according to Example 4 and containing 0.005% bromadiolone was investigated.

Both feeding containers were weighed and filled with the rodenticide product, in an amount sufficient for the daily needs of the rats. After 24 hours, both feeding containers (plus the spilled feed) were weighed again and the total amount of the rodenticide product consumed by each rat was calculated. This was repeated for five consecutive days and the results were averaged.

The following results were obtained: on average, the consumption rate of the paraffinized blocks having the same composition as the solid part of the claimed rodent control device was 33.65% in comparison with the average consumption rate of the EPA Standard (66.35%). On average, the consumption rate for the bait having the same composition as the pulpy part of the claimed rodent control device was 33.60% in comparison with the average consumption rate of the EPA Standard (66.40%). In case of the combined product according to the invention, the consumption rate increased to 55.4%, while the consumption of the EPA Standard decreased to 44.6%.

The initial high consumption rates of the EPA Standard are due to its better taste, and the absence of paraffin, colouring agents, active ingredients, repellents, preservatives etc. Rodents consumed the pulpy part at the same rate as the solid part which may be due to the fact that the solid part of the claimed rodent control device is also sufficiently attractive, and that the pulpy part used in the studies was less acceptable than average because of the uneven quality of the mostly food-like raw materials used for its production.

In case of rodenticide baits, the approximately 33% consumption rate in comparison with the EA Standard is a very good result considering the 20% lower acceptance/palatability limit, although lower acceptance/palatability can also be convenient provided that the mortality is 100% in the end of the study. The data clearly demonstrate that rodents preferred the combination according to the invention over the EPA Standard and this is the reason for the reduction in the consumption of the EPA Standard in the third study. This may be due to the fact that in contrast with the monotonous EPA feed, the combined bait offers variability via the pulpy and solid part.

The mortality was 100% in all of the above mentioned studies.

The invention claimed is:

1. A rodent control device, which comprises a rodenticide bait comprising a combination of a solid and a pulpy part, wherein the solid part is a shaped paraffinized rodenticide bait with a rodenticide concentration lower than that of the combination, said solid part comprising at least one hole for containing the pulpy part having a rodenticide concentration higher than that of the combination.

2. A rodent control device, which comprises a rodenticide bait comprising a combination of a solid and a pulpy part, wherein the solid part is a shaped paraffinized rodenticide bait with a rodenticide concentration equal to that of the combination, said solid part comprising at least one hole for containing the pulpy part having a rodenticide concentration equal to that of the combination.

3. The rodent control device according to claim 1, wherein the percentage of the solid part is 70-90 and the percentage of the pulpy part is 10-30 compared to the total mass of the device.

4. The rodent control device according to claim 1, wherein the rodenticide in both the solid and the pulpy part is an acute rodenticide selected from the group consisting of scilliroside, strychnine, crimidine, bromethalin, sodium fluoroacetate, fluoroacetamide, zinc phosphide, norbormide, thallium sulphate, alpha-chloralose, alpha-naphthyltiourea and mixtures thereof.

5. The rodent control device according to claim 1, wherein the rodenticide in both the solid and the pulpy part is a chronic rodenticide.

6. The rodent control device according to claim 5, wherein the chronic rodenticide is a first generation anticoagulant selected from the group consisting of warfarin, warfarin sodium, coumachlor, coumatetralyl, coumafuryl, pivaldione, diphacinone, chlorophacinone and mixtures thereof.

7. The rodent control device according to claim 5, wherein the chronic rodenticide is a second generation anticoagulant selected from the group consisting of bromadiolone, diphenacoum, brodifacoum, difethialone, flocoumaphen and mixtures thereof.

8. The rodent control device according to claim 1, wherein the rodenticides in the solid and the pulpy part are different.

9. The rodent control device according to claim 8, wherein the different rodenticides are first generation and second generation anticoagulants.

10. The rodent control device according to claim 2, wherein the shaped rodenticide bait comprises a fixing hole.

11. The rodent control device according to claim 2, wherein the shaped rodenticide bait is an extruded block with a rectangular cross-section comprising at least one hole for accommodating the pulpy part.

12. A method for the preparation of the rodent control device according to claim 1, comprising the steps of:
 (i) preparing the solid part with at least one hole for accommodating the pulpy part with paraffin wax, and the rodenticide;
 (ii) preparing the pulpy part with the rodenticide; and
 (iii) filling part or the whole of at least one hole in the solid part with the pulpy part during or after the preparation of the solid part.

13. A method of controlling rodents, which comprises placing the rodent control device according to claim 1 in a location frequented by said rodents.

14. The method according to claim 13 for the control of rodents belonging to the family of murine animals (Muridae), selected from the group consisting of house mouse (*Mus musculus*), steppe mouse (*Mus spicilegus*), striped field mouse (*Mus agrarius* Pall), black rat (*Rattus rattus*) and brown rat (*Rattus norvegicus*).

15. The method according to claim 14, wherein the rodent is a black rat or brown rat.

16. The rodent control device according to claim 2, wherein the percentage of the solid part is 70-90 and the percentage of the pulpy part is 10-30 compared to the total mass of the device.

17. The rodent control device according to claim 2, wherein the rodenticide in both the solid and the pulpy part is an acute rodenticide selected from the group consisting of scilliroside, strychnine, crimidine, bromethalin, sodium fluoroacetate, fluoroacetamide, zinc phosphide, norbormide, thallium sulphate, alpha-chloralose, alpha-naphthyltiourea and mixtures thereof.

18. The rodent control device according to claim 3, wherein the rodenticide in both the solid and the pulpy part is an acute rodenticide selected from the group consisting of scilliroside, strychnine, crimidine, bromethalin, sodium fluoroacetate, fluoroacetamide, zinc phosphide, norbormide, thallium sulphate, alpha-chloralose, alpha-naphthyltiourea and mixtures thereof.

19. The rodent control device according to claim 2, wherein the rodenticide in both the solid and the pulpy part is a chronic rodenticide.

20. The method according to claim 12, wherein step (i) is by extrusion and step (iii) is by coextrusion.

21. The rodent control device according to claim 1, wherein the shaped rodenticide bait comprises a fixing hole.

22. The rodent control device according to claim 1, wherein the shaped rodenticide bait is an extruded block with a rectangular cross-section comprising at least one hole for accommodating the pulpy part.

23. The rodent control device according to claim 19, wherein the chronic rodenticide is a first generation anticoagulant selected from the group consisting of warfarin, warfarin sodium, coumachlor, coumatetralyl, coumafuryl, pivaldione, diphacinone, chlorophacinone and mixtures thereof.

24. The rodent control device according to claim 19, wherein the chronic rodenticide is a second generation anticoagulant selected from the group consisting of bromadiolone, diphenacoum, brodifacoum, difethialone, flocoumaphen and mixtures thereof.

25. The rodent control device according to claim 2, wherein the rodenticides in the solid and the pulpy part are different.

26. The rodent control device according to claim 25, wherein the different rodenticides are first generation and second generation anticoagulants.

27. A method for the preparation of the rodent control device according to claim 2, comprising the steps of:
 (i) preparing the solid part with at least one hole for accommodating the pulpy part with paraffin wax, and the rodenticide;
 (ii) preparing the pulpy part with the rodenticide; and
 (iii) filling part or the whole of at least one hole in the solid part with the pulpy part during or after the preparation of the solid part.

28. The method according to claim 27, wherein step (i) is by extrusion and step (iii) is by coextrusion.

* * * * *